(12) United States Patent
Appleby (10) Patent No.: US 6,621,086 B1
(45) Date of Patent: Sep. 16, 2003

(54) RADIOCHROMIC IMAGING METHOD

(75) Inventor: Alan Appleby, Middlesex, NJ (US)

(73) Assignee: Rutgers, The State University of New Jersey, New Brunswick, NJ (US)

(*) Notice: Subject to any disclaimer, the term of this patent is extended or adjusted under 35 U.S.C. 154(b) by 0 days.

(21) Appl. No.: 09/569,342

(22) Filed: May 11, 2000

(51) Int. Cl.[7] .............................................. A61N 5/00
(52) U.S. Cl. ................................... 250/492.1; 250/580
(58) Field of Search ........................ 250/492.23, 473.1, 250/474.1, 484.3, 253, 398, 400, 472.1, 475.2, 492.1, 208.1, 341.7

(56) References Cited

U.S. PATENT DOCUMENTS 3,449,572 A * 6/1969 Sylvester et al. ......... 250/474.1
5,430,308 A * 7/1995 Feichtner et al. ......... 250/475.2
6,103,316 A * 8/2000 Tran et al. ................ 427/208.4
6,403,311 B1 * 6/2002 Chan .......................... 435/375

* cited by examiner

Primary Examiner—John R. Lee
Assistant Examiner—Christopher M. Kalivoda
(74) Attorney, Agent, or Firm—Salzman & Levy (57) ABSTRACT

The present invention relates to radiochromic imaging methods for generating a permanent colored spatial representation of an irradiation pattern wherein the intensity of the color in the image correlates to the dose level of irradiation, and more particularly to a method that provides representations of the quantity and position of radiolabelled polymeric materials separated by chromatographic techniques and furthermore, to a method that provides a two or three dimensional colored image correlating to a dosimetric pattern supplied by an external or embedded source.

25 Claims, 3 Drawing Sheets

RADIOCHROMIC IMAGING METHOD

FIELD OF THE INVENTION

The present invention relates to radiochromic imaging methods for generating a permanent, colored two or three dimensional spatial representation of an irradiation pattern wherein the intensity of the color of the image correlates to the dose level of irradiation, and more particularly to methods of utilizing these imaged color changes in applications such as tissue-equivalent dosimeters for medical radiotherapy to assess precise radiation targeting within a patient and in-other applications such as chromatographic analysis to determine the location and quantity of separated components.

BACKGROUND OF THE INVENTION

Quantification of objects in a given environment has been a longstanding requirement since man has been able to count. Beside the obvious need in commerce to know how many of one item might be traded for another, there are many other areas where quantification plays an important role. For example, in the physical sciences, quantification of exposure to chemicals or radiation, or dosage of medicine all play a role in our well being. Even when no direct contact with these materials is an issue, quantification plays an important role in analytical testing for these materials.

Quantification can be performed directly (i.e., by counting the objects of interest) or indirectly (i.e., by correlating the number of objects to some other measurable parameter).

Indirect quantification has been widely used in correlating the intensity of color to the quantity of a substance. In spectroscopy the relationship is defined by Beers Law. Simply stated, there is typically a correlation between the amount of a given material and the intensity of light absorbed by that material. If the absorbed light is of a given wavelength or range of wavelengths within the visible spectrum then the absorption of this light creates color.

It has also been known that the interaction of electromagnetic radiation and matter can create new chemical materials. In some cases the new material will be colored. It is then possible to correlate the three parameters: amount of radiation, amount of reactant matter, and intensity of coloration of the product. In this manner if two of the three parameters are known then the third can be quantified indirectly. Studies of this kind can be conducted either over time or space to obtain a temporal and/or spatial quantification of either the amount of radiation or the amount of the reactant material if the intensity of the coloration can be determined.

Chromatographic techniques for separating multicomponent mixtures has been an invaluable tool to the scientific community. Such techniques provide the ability to not only separate but also quantify and ultimately identify the various components in the mixture. Depending on the specific chromatographic technique many different types of materials can be separated from one another even though they may be structurally very similar. Such materials include anionic and cationic ions, simple organic molecules and more complex organic polymers. These polymers may be synthetically derived as is the case with polyesters, polyethers, or polyolefins or may be naturally produced as are proteins, polynucleotides, or complex starches and carbohydrates. Separation methods can be based on chemical or physical properties such as electronic charge, chemical reactivity, molecular mass, or molecular volume.

In virtually all cases, the mixture to be separated must be incorporated in a system that has a mobile phase and a stationary phase. The mobile phase carries the individual components across the stationary phase and may consist of gas, a liquid, or mixtures thereof. Most commonly inert gases such as nitrogen, helium, carbon dioxide or the like are used. Common liquids include pure water, salt-containing water, organic solvents and mixtures thereof.

The stationary phase may be composed of materials that are either inertized or activated and may be derived from synthetic or natural materials. The critical factors in selecting a stationary phase are that it must be essentially stable over time and not be soluble in the mobile phase. Another important attribute of the stationary phase is that it provide sufficient adsorption of the individual components to effect separation. This is typically achieved by having the stationary phase comprise very small particles having a large surface area or in some cases to have the stationary phase have hollow portions that the individual components must migrate.

Many materials can be employed for use as a stationary phase including insoluble salts, clays, talc, polyolefins, resins, and the like. The interaction of the individual components with the mobile phase and the stationary phase causes the individual components to migrate through the stationary phase at different rates, thereby causing them to separate. Separation is thus obtained by each component having a unique rate of migration. In a fairly recent innovation the stationary phase and the mobile phase can actually be reduced to one phase. In this case the stationary phase is in the form of a polymeric material dissolved in the mobile phase to essentially form a gel material. In the gel the stationary phase does not migrate, especially if the stationary phase polymeric material is crosslinked. In this system there is an extremely high propensity for interaction of the individual components with the stationary phase since contact is essentially made with individual molecules of the polymeric stationary phase. Bulk effects that would limit interaction of the individual components and the stationary phase are essentially eliminated.

The flow of the mixture to be separated is achieved by having the mobile phase flow either under gravity or pressure or by diffusion from an inlet side to an outlet side. More recently a technique that does not require the mobile phase to physically flow has been achieved. In this method the mixture is dissolved in the mobile phase and the stationary phase is placed in a environment that subjects the system to an electric current and the components in the mixture are separated due to their electrical charge and the interaction with the stationary phase. One such method is electrophoresis, wherein substances disposed within a gel are subjected to an electrical current. These substances migrate in the gel, under the influence of an electrical field.

Unless the components in the mixture are inherently colored, visualization of the separated components requires an additional step. This can be achieved without the need of other materials by such techniques as measuring spectroscopic absorbtivity in the ultraviolet or infrared region of the components themselves. In other techniques color formers are applied to the migrated components to generate color regions. Coloring the substances with a dye reveals their migrated position within the gel. This electrophoretic method is used in present day DNA and protein analyses. A problem common to DNA testing, or electrophoretic methods, is the overlap of certain migrating substances within the gel. Those overlapping substances cannot be easily distinguished from each other. Other problems that typically arise when employing chromatographic techniques is that even when coloring has successfully identified the location of the various components, the color fades with time. This is of particular concern if the object is to quantify the amount of each component using the intensity of the color to correlate to the quantity of the component.

The quantification of radiation exposure has been performed directly using such tools as Geiger counters. Techniques of this type provide basically bulk information and cannot be used for determining the irradiation level at various depths within a subject material. In other words a three dimensional, spatial profile of irradiation dose is not feasible with such direct techniques. This type of information, however, is invaluable in such areas of science as radiation therapy and food sterilization.

It is critical in medical radiotherapy that the exact radiated area in the body, or exact direction of a radiation beam, with respect to a patient is known. Patients being irradiated with beams of high dosages of radiation can be severely harmed if the radiation direction or its ultimate direction is not precisely known. For example, a tumor located near a sensitive body organ, such as a spinal cord, must be precisely irradiated. Any radiation misalignment can cause damage to the spinal cord, with the unintended result of severely and permanently injuring the patient. The simulation gel of the present invention is irradiated to determine the precise extent of the volumetric distribution of radiation which the beam will target.

Recent advances in computer and radiation delivery techniques have increased the need to precisely define the radiation target volume. Radiotherapy methods are now more sophisticated, resulting in a need for more detailed information about the typically more complex radiation dose distribution than was previously the case. These treatment modalities include high dose-rate, or highly directed types such as conformal (CRT), intensity-modulated (IMRT), brachytherapy, pencil-beam, and stereotactic radiotherapies.

The common aim of these new methods is to deliver relatively high radiation doses to malignancies, within narrowly prescribed physical margins to spare surrounding normal tissues. In order to achieve beneficial results without increasing the morbidity rate, an extraordinary investment in terms of professional-time and effort must be made in the quality assurance and treatment planning processes. These processes could be facilitated by new techniques for three-dimensional radiation dosimetry.

Several years ago a tissue-equivalent system was developed for radiation dose distribution studies, that was capable of being imaged by optical scanning. The system consisted of an aqueous agarose gel (1%) that contained ferrous ions and xylenol orange. Radiation-chemical reactions initiated in the water component disposed in the gel, caused a chain reaction oxidation of 2-valent ferrous ions, which were converted to 3-valent ferric ions. The reaction was contained in local concentrations proportional to the local radiation dose deposited. It was already established that the ferric ion distribution could be imaged by MRI techniques, as a consequence of the paramagnetic nature of the ferric ions. The presence of xylenol orange allowed the rapid formation of a colored complex between ferricions and xylenol orange. This provided the possibility of using three-dimensional imaging via optical scanning techniques. This technique was potentially much more cost-effective and convenient than MRI.

More recently, a simple optical scanning method was developed. The newer method used a CCD camera for three dimensional imaging of the dose distributions of the radiated ferrous/xylenol orange gel. Advantages of such an aqueous-based system like this, was its ease of preparation, and non-toxicity.

A major disadvantage of the aqueous ferrous/xylenol orange system, was the quickly degrading image that resulted from the diffusion of the colored radiation-induced complex. It was, therefore, necessary to accelerate the scanning procedure. This was problematic when low dose rates and hence, long irradiation times were needed. It was also difficult with small sized irradiated fields, where small amounts of diffusion represent large proportional losses of image coherence.

Another prior art three-dimensional dosimetry system is one based on radiation-induced polymerization of acrylamide gels. The gels turn from transparent to milky white following exposure to radiation, and were scanned optically. The images did not degrade by diffusion. This system had the disadvantages of greater complexity of preparation (oxygen had to be rigorously excluded). Toxicity of the acrylamide monomer also posed concomitant disposal problems. The attenuation was dependent upon scattering, rather than by absorption, of the radiation, thus limiting the sensitivity.

It is one object of the method of this invention, to provide a color forming reactant that on exposure to radiation generates a color.

It is yet another object of the invention to provide a source of radiation that causes a color forming reactant to generate a colored product.

It is another object of the method to incorporate a color forming reactant into a matrix or stationary phase.

It is still another object of the invention to provide a process for forming a colored image that is insensitive to the presence of oxygen.

It is yet another object of the method for the colored product formed by irradiating the color forming reactant in a matrix of elements, constituting a defined shape and volume, to spatially quantify the amount of radiation that is absorbed within each element of the matrix.

It is still another object of the invention to provide a tissue-equivalent dosimeter that provides a stable image that is directly related to radiation dose.

It is yet another object of the method, that a radioactive label is tagged into individual members a chemical mixture. The mixture is subjected to a chromatographic system having a color forming reactant uniformly present in the matrix such that after separation the radiolabel tag will generate color at the migration site. The level of radiation will be used to quantify the amount of each individual component.

SUMMARY OF THE INVENTION

In accordance with the present invention, a system has been developed that provides a stable color representation from the interaction of radiation and a color forming agent. The color representation in a given spatial area or volume accurately correlates to the radiation dosage impinging on the color forming reactant in the spatial area or volume of the matrix.

In one series of embodiments the radiation is supplied by an external source and exposes the color forming reactant present in either a two or a three dimensional dosimeter matrix. The quantification of optical density within the respective units of pixels or voxels of the matrix accurately correlate to their level of radiation absorption.

In a second series of embodiments the radiation is supplied by radiolabel tagging the individual components in a mixture and having the color forming reactant uniformly disposed throughout a stationary substrate. Subsequently, a chromatographic technique is performed to separate the components, allowing the radioactive label in each migrated component to cause color formation in the area of migration.

The current invention reflects the discovery that better quantification can be obtained in electrophoretic methods and radiation testing with the use of specific tetrazolium salts. Tetrazolium salts have been long used as biological indicators. There is considerable literature on the use of tetrazolium compounds as radiochromic dosimeters.

In aqueous solution, these soluble compounds are reduced by radiation to highly colored, insoluble compounds, known as formazans. There are at least two hundred and forty different tetrazolium compounds, and four hundred and fourteen formazans. An example of a tetrazolium compound that can be used as a radiochromic dosimeter is nitro blue tetrazolium (NBTZ). This compound has the following structure:

(1)

Reduction of NBTZ leads to the colored formazan, depicted below:

(2)

A necessary characteristic of the color indicators of this invention, is their conversion from soluble to insoluble substances in water along with the color change. As aforementioned, one of the unique characteristics of the above tetrazolium compound is that the resulting formazan molecule, produced by radiation, changes both its color and solubility. In an aqueous gel, the formazan would not diffuse freely through the aqueous medium as do soluble materials such as the ferric/xylenol orange complex. Instead it attaches to surfaces, such as the surface of the gel structure. This forms the basis of a non-diffusing image of the radiation dose in three dimensions, in an aqueous non-toxic medium.

It is an aspect of this invention to provide an improved method of producing a radiochromatic change within a gelatinous material.

It is another aspect of the invention to provide a radiochromatic method whereby a precise location of a substance disposed within a gel can be determined.

It is a further aspect of this invention to provide a radiochromatic method whereby the migration of substances within a gelatinous medium can be precisely determined.

BRIEF DESCRIPTION OF THE DRAWINGS

A complete understanding of the present invention may be obtained by reference to the accompanying drawings, when considered in conjunction with the subsequent detailed description, in which.

Other benefits and further scope of applicability of the present invention will become apparent from the detailed description given hereinbelow. It should be understood, however, that the detailed description and specific examples, while indicating preferred embodiments of the invention, are given by way of illustration only, since various changes and modifications within the scope and spirit of the invention will become apparent to those skilled in the art from this detailed description.

DESCRIPTION OF THE PREFERRED EMBODIMENT

Generally speaking, the invention features radiochromic methods for use in such diverse technical applications as radiation therapy and electrophoretic separation techniques. The first radiochromic method comprises the steps of: a) preparing a chemical matrix for testing; b) inserting into the chemical matrix of step (a), an aqueous soluble, color forming compound; and c) irradiating the aqueous soluble, color forming compound of step (b) in order to produce a color change in said aqueous soluble, color forming compound, and in order to change its solubility within the chemical matrix.

In a first embodiment of the present invention for use in a radiation therapy application (described supra), the chemical matrix typically comprises a gel composition that can simulate mammalian soft tissue. Common water based-translucent gels such as agarose, carrageenan, cellulosics, carboxymethyl guar gum, starch derivatives, polysaccharides such as dextran, mixtures of gel forming gums such as locust bean gum and xanthan gum, or gelatin gels are typically used. Above certain concentrations, the gels have some properties similar to solids and the gel objects can be sufficiently rigid so as to maintain a given shape or alternatively can be supported in a vessel to maintain a desired two dimensional (i.e., coating) or three dimensional shape. Irradiation of these color forming compound-containing gels is then performed. In a special application where the gel object is in a two dimensional gel matrix, irradiation is typically applied from a single direction (e.g., perpendicular) to the surface of the two dimensional gel matrix and the intensity of coloration within a given pixel is measured and correlated to the amount of radiation absorbed by each given pixel. In this scenario, the coating may be used to produce an image-based on the intensity of the impinging irradiation from a direction that is vertical or obliquely angled to the coating surface. Although this embodiment has significant utility, the preferred embodiment of the present invention employs a three dimensional gel matrix.

In the case of a three dimensional gel matrix irradiation can be provided-either from a single direction or multiple directions especially including multiple irradiation sources. The intensity of coloration at a given volume element (voxel) within the gel matrix will depend on the amount of radiation absorbed, in the case of multidirectional irradiation the summation of the radiation from all directions impinging on a voxel will determine the intensity of the final coloration. In one sense this embodiment diverges from the prior art in which color forming tetrazolium agents are used in traditional dosimeters in order to measure the extent of irradiation over a period of time, with no consideration being given to direction or spatial configuration of the incoming irradiation source. Especially for the three dimensional gel matrix, this approach can be used to accurately model the precise location that a series of radiation beams will target within a human body.

In pencil-beam or sterotactic radiotherapy, it is preferred that the cross-sectional area of the irradiating beam or beams be as small as possible in order to provide sufficient resolution to accurately determine both the target and any unwanted spreading of radiation beam.

The irradiation beam or beams may be used in a static mode and therefore have a fixed geometry relative to the tissue-equivalent gel matrix or may be positioned in numerous locations during the course of the irradiation. This latter, dynamic, mode would be used to simulate conformal radiation therapy where the object is to maximize the radiation targeted at a diseased site while minimizing the deleterious effects on the healthy tissues at the margin. If multiple locations are desirable, the beam is preferably scanned in a Raster imaging mode (i.e., along a linear pathway from a chosen start point to a chosen end point and then repositioned a distance vertically removed from the first linear pathway and then a second linear pathway parallel to the first is produced, the vertical distance is determined by the cross-section of the beam and the desire to maintain irradiation dose uniformity across this irradiation array).

The irradiation beam can also be modulated temporally and can be set to various on/off frequencies as well as modulated by cross-sectional area. Again, the object is to provide the maximal radiation intensity to the diseased tissue while causing minimal damage to surrounding healthy tissue.

If more than one irradiation beam is employed, one embodiment of the invention allows for the beams to impinge the object essentially simultaneously or within the same time frame while a second embodiment allows for the signals to impinge at times totally independent of one another.

The present invention provides the best and most direct method of simulating a given radiation therapy regimen in a human patient in order to reduce injurious effects of the treatment. In addition to determining the regime of irradiation this invention also allows a process for quality control of the irradiation equipment (i.e., to establish that the irradiation dosages are correctly calibrated).

The second application for the present invention is in the area of chromatography. As is well known, there is a long history on the need for isolating and identifying the number and quantity of components in a mixture. Chromatographic techniques allow a method of separating materials within a mixture but typically do not provide a method for quantification of those components. Typically, this is performed as a separate step and may require extraction of the separated components from the chromatographic process before the quantification can be made. Any additional steps in quantification, especially which are not in situ, tend to create the possibility for error (i.e., transfer error). The present invention allows for a process that allows quantification in situ thus eliminating potential transfer errors.

This second radiochromic application comprises the steps of: a) preparing a chemical matrix for testing; b) inserting into the chemical matrix of step (a), an aqueous soluble, color forming compound; c), placing a mixture of materials at either a starting point or along a line within the chemical matrix (the materials in this experiment must be radiolabelled); d) separating the mixture from (c) using chromatographic techniques; and e) allowing sufficient time for the migrated radiolabelled components to irradiate and cause a change in the solubility and color of the neighboring color forming compound within the chemical matrix.

In a first embodiment to the second application described supra, the chromatographic technique comprises an electrophoretic process. The migration of the individual components of the mixture is not dependent on the active transport of a mobile liquid phase, but rather uses an electric current to transport charged components at varying distances dependent on their absolute charge.

In a second embodiment to the second application, described supra, the chromatographic technique is a process that employs an active transport mobile phase, such techniques as high performance liquid chromatography and gel permeation chromatography are recommended. In this case the color forming compound is either present in the mobile phase by continuously being added to the stationary phase or is chemically bound to the stationary phase. In either case, there must be a uniform concentration of the color forming compound throughout the stationary phase and matrix.

The methods of the second embodiment are directed towards an improved quantitative chromatographic technique for polymeric materials especially those found in biological systems (e.g., proteins and polynucleic acids such as DNA or RNA). In these cases, the polymeric systems typically have numerous components that are very similar in chemical composition and molecular weight and therefore tend to migrate in similar fashion. It is extremely important then that close, somewhat overlapping bands of components be resolved from one another if true quantification is to be achieved. Using radiolabelled components and their radiation to develop a colored image which can then be accurately quantified, is a superior attribute of this methodology.

Essentially any radionuclide can be used in the present invention as a radiolabel with the proviso that they do not modify the chemical and physical properties of the polymer (e.g., destroy the native structure of the polymer or substantially alter the electrical charge of the polymer. Preferred radiolabels within the polymers of the present invention include any isotopes that yield beta, low energy gamma or alpha radiation, for example, $^3$H, $^{14}$C, $^{32}$P, $^{33}$P, $^{35}$S, and 125I.

The current invention comprises the use of tetrazolium salts. Tetrazolium salts have been long used as biological indicators, and there is considerable literature on the use of tetrazolium compounds as radiochromic dosimeters.

In aqueous solution these soluble compounds are reduced by radiation to highly colored, insoluble compounds, known as formazans. There are large number of known tetrazolium compounds. They are all useful in the current invention as long as they meet the criteria of being able to be uniformly dispersed in the chemical matrix or array and they have the ability to generate formazans on exposure to radiation. As for the resulting formazans an equally large number are known and they should have the property of being insoluble in the chemical matrix, stable over time and afford a high optical extinction coefficient (i.e., generate intensely colored structures)

Experiments were conducted using a tetrazolium compound called is nitro blue tetrazolium (NBTZ). This compound has the following structure:

(1)

Reduction of NBTZ leads to the colored formazan, depicted below:

(2)

A necessary characteristic of this and other contemplated color forming compounds of this invention, is their conversion from soluble to insoluble substances in water along with the color change when irradiated. In an aqueous gel, the resultant formazan would not diffuse freely through the aqueous medium, as do soluble materials such as the ferric/xylenol orange complex. Instead it will attach to surfaces, such as the surface of the gel structure. This forms the basis of a non-diffusing image of the radiation dose in three dimensions, in an aqueous non-toxic medium.

Since the process of formazan formation from the tetrazolium salts involves overall chemical reduction, the presence of oxidizing species will deleteriously affect overall yield of the formazan colorant. It is well known that high-energy irradiation of aqueous solutions generate hydrated electrons which in some circumstances can ultimately convert to strongly oxidizing radicals such as the hydroperoxy radical, —$O_2^-$. This can occur when molecular oxygen is present in solution. It is anticipated that this process will impact the yield of the formazan colorant formation either by preventing its formation or alternatively decomposing the formazan product. It is expected that a sufficient concentration of a tetrazolium salt such as nitro blue tetrazolium, that reacts rapidly with hydrated electrons, will effectively prevent the formation of hydroperoxy radicals in air-saturated aqueous solutions. Another oxidising product of the interaction of high energy radiation with water is the hydroxy[11] radical, —OH. It is anticipated that this radical will similarly impact the yield of formazan product either by preventing its formation or alternatively decomposing the formazan product. It has been found that materials that will "quench" or decompose the hydroxy radical prior to its involvement with the tetrazolium/formazan couple will significantly improve the yield of the formazan colorant as measured by optical density. Such additives to increase the radiation-chemical yield of the formazan include materials that will themselves be oxidized (sacrificial oxidants) (i.e., reducing agents). Because of the very strong oxidizing property of the hydroxy radical even weak reducing agents will be effective at quenching the hydroxy radical. One class of reducing agents contain labile, abstractable hydrogen atoms such as from alkanes, alkenes (especially allylic or benzylic hydrogens), and derivatives therefrom. Especially useful derivatives include carboxylic acids, alcohols, ethers or mercaptans. For example, abstractable hydrogens are found on carbon atoms adjacent to heteroatoms such as nitrogen or oxygen, e.g., the methylene hydrogen in benzylic alcohol. Other examples include mercaptan hydrogens in which the thiol groups ultimately form disulfide linkages.

In the present invention, such materials must not only react with the hydroxy radical but must not cause other deleterious effects such as solubilization of the product formazan. Therefore, the use of low molecular weight alcohols is not recommended. However, higher molecular weight derivatives may be beneficial for yield enhancement. Without being bound by the foregoing theory, it has been found that Triton X-100 (a polyethylene glycol derivative of nonyl phenol) causes a substantial improvement in formazan yield. At concentrations up to 0.1 Molar in Triton X-100 overall formazan yields are increased, based on optical density values, by a factor of approximately 3.

It has also been discovered that salts of carboxylic acids also increase the yield of the formazan colorant. The carboxylic acid salts suitable for the present invention include salts that are water-soluble such as lithium, sodium, potassium, and unsubstituted or substituted ammonium salts. Abstractable hydrogens can come from either the alkyl backbone or in the case of formate salts, from the hydrogen attached to the carbonyl carbon. For example, the addition of up to 0.5 Molar sodium formate, increased the formazan yield by a factor of 4 fold based on optical density values. Unexpectedly, the yield is further improved with simultaneous use of both sodium formate and Triton X-100. The improvement is at least additive and may be synergistic, but it is certainly not competitive. For example, the addition of 0.005 Molar Triton X-100 and 0.5 Molar sodium formate increase the overall rate by a factor of 15 (see FIG. 8). Without being bound by theory the following mechanism is suggested to account for the improved process:

$$T^{++} + e^- \rightarrow .T^+ \quad (1)$$

$$T^{++} + .H \rightarrow .T + H^+ \quad (2)$$

$$.OH + GH_2 \rightarrow .GH + H_2O \quad (3)$$

$$.T^+ + .GH + H^+ \rightarrow T^{++} + GH_2 \quad (4)$$

$$.T^+ + .T^+ \rightarrow F^+ + T^{++} \quad (5)$$

$$.OH + DH_2 \rightarrow .DH + H_2O \quad (6)$$

$$.OH + HCOO^- \rightarrow .COO^- + H_2O \quad (7)$$

$$.T^{++} + DH_2 \rightarrow F^+ + .DH_2 \quad (8)$$

$$.COO^{31} + T^{++} \rightarrow .T^+ + CO_2 \quad (9)$$

In equations 1 through 9;

.OH=hydroxy radical; e$^-$=hydrated electron;

T$^{++}$=tetrazolium salt; .T$^+$=tetrazolium radical;

.H=hydrogen radical; H$^+$=proton;

GH$_2$ =gelatin; .GH=gelatin radical;

DH$_2$ =Triton X-100; .DH=Triton X-100 radical;

HCOO$^-$=formate ion; .COO$^-$=formate ion radical; and

F$^+$=formazan product.

In the absence of additives such as Triton X-100 and sodium formate, reactions 1 through 5 occur and the hydroxy radical abstracts a hydrogen atom from the gelatin molecule. The gelatin radical has sufficient oxidative activity to return the tetrazolium radical cation back to the original tetrazolium salt. This side reaction process creates an inefficiency which is observed by having a reduced level of formazan formation per unit impinged radiation. In the presence of either Triton X-100 or sodium formate reactions 6 through 9 are also allowed. In the case of reaction 6, the Triton X-100 loses a hydrogen radical to quench the hydroxy radical and now in this case-the thus formed Triton X-100 radical (polyethoxylated nonyl phenol radical) does not cause the re-oxidation of the tetrazolium radical cation. In the case of reaction 7, the formate ion quenches the hydroxy radical in a redox reaction that generates a formate radical anion which likely loses another electron to a tetrazolium salt to generate yet another tetrazolium radical cation. In this latter case the yield of the formazan dye, is actually increased beyond the normal radiochemical process yield.

Alternatively, the effect of Triton X-100 can be explained by migration of the tetrazoinyl radical into the hydrophobic region of the detergent micelles. In that location the radicals would have higher local concentrations and would be more likely to form formazan product (by second order dismutation reaction, reaction 5 in the patent document) than undergo alternative reactions in aq. phase that would give less formazan, or even reoxidation to the tetrazolium salt. Under these circumstances any material that forms a stable micelle and does not destroy the stability of the tetrazoinyl radical should assist the formation of the desired formazan product. Specifically contemplated as useful micelle formers is the general class of detergents or surfactants that have both a hydrophilic and hydrophobic moiety. In this regard, surfactants which are either nonionic, anionic or cationic have utility in the present invention. Particularly preferred are nonionic and cationic surfactants. These surfactants will not cause potential electronic attraction as might be the case between an anionic surfactant and the positively charged tetrazoinyl radical.

Another class of compounds useful as quenching agents for the hydroxy radical are compounds that are themselves stable radicals. Examples of such materials include ferrous ions, cerous ions, and nitric oxide.

Prior art describes a tetrazolium compound in ethyl alcohol solutions used as radiochromic dosimeter. Aqueous-ethanol solutions of NBTZ are also described for high dose radiation dosimetry. However, the formazan product is soluble in ethanol, so that for the applications of the present invention, which requires an essentially non-diffusing colorant in order to correlate color intensity to absorbed radiation within a pixel or voxel, these prior art references are not useful and in fact are detrimental to the utility of the present invention.

It is also expected that other detergent/surfactant similar to Triton X-100 will have similar enhancing effects as Triton X-100. The enhancing effects of detergents upon the reduction of tetrazolium salts by xanthine oxidase plus xanthine has been reported. This effect was attributed to decreases in susceptibility to inhibition by superoxide dismutase or oxygen. Such an attribution is not relevant to the present invention which does not employ enzymatic reduction.

The nature of the radiation to effect the chemical reaction of the tetrazolium salts to the formazans, can be any type of ionizing radiation. This includes such particles as alpha and beta particles and x-rays, gamma rays, cosmic rays, electron beams, and near and far ultraviolet radiation. Typically, radiation doses in the range of 10 to 1000 Gray are utilized in the present invention but the invention is not limited by such a range. The preferred dosage will be dependent upon the precise color forming compound selected as well as its concentration within the matrix and the presence of added compounds designed to change the radiation-chemical yield of the colored formazan.

The following experiments describe the preparation and tests performed on the gels of this invention, and the results of the-testing of the gels in accordance with the accompanying FIGURES. Clinical irradiations were conducted at the Radiology department of White Plains Hospital.

Experiments:

Aqueous gelatin gels (4% gelatin, neutral pH) containing dissolved NBTZ, were prepared, as follows: NBTZ was dissolved in-the appropriate volume of deionized water for the desired concentration, at room temperature. Gelatin powder was slowly added, with stirring, to achieve the 4% concentration, and the mixture heated to 45 degrees C., with continued stirring. After the gelatin dissolved, the pale yellow solution was cooled to 40 degrees C., and transferred to optical cuvettes of 1 cm. optical path length. The cuvettes were kept refrigerated in dark storage prior to being irradiated with gamma rays at doses approximately between 15 and 800 Gray.

Figure 1:
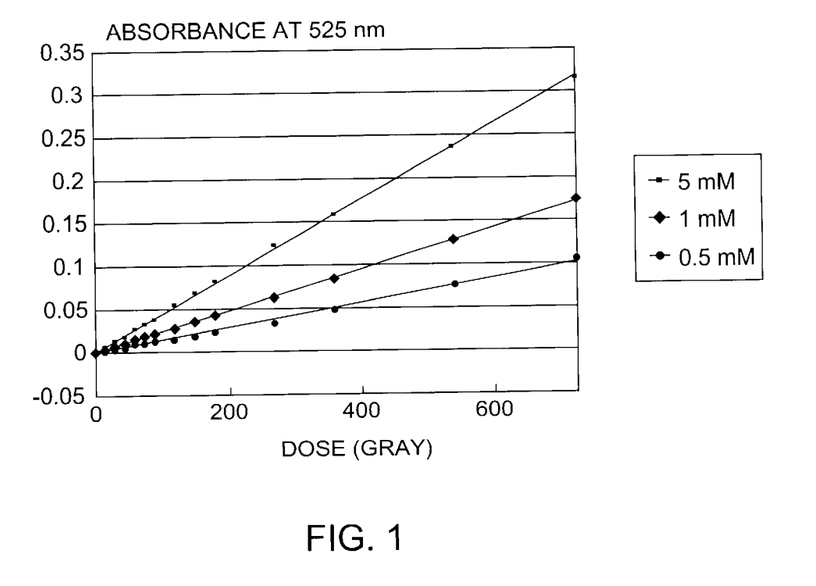
FIG. 1 illustrates a graphical view of absorption at a wavelength of 525 nm versus dosage for gels containing three different concentrations of NBTZ.

Now referring to FIG. 1, the optical absorption at 525 nm wavelength (unirradiated blank subtracted) is shown as a function of radiation dose at three NBTZ concentrations. It is observed that there is no fading of the optical absorption in these cuvettes during two weeks postirradiation storage at room temperature. It was also found, that there was no effect of removing dissolved oxygen by bubbling nitrogen gas through the gelatin solution prior to gelation.

Based on these experiments a NBTZ concentration was selected of 1 mM, for studying phantoms of clinical size. Gels were formed in cylindrical glass jars of a size 9.2 cm diameter, and 15 cm. height, and irradiated with external beams of clinical photons (6 MV) from a Varian Clinac 2100 EX accelerator in a cruciform pattern, perpendicular to the cylinder axis.

A irradiation beam of 3 cm.×3 cm., was used to deliver a dose of 450 Gray to isocenter, followed by a similar beam at right angles to the first, for an additional dose of 250 Gray to isocenter, for a total dose of 700 Gray. Exit dose of this second beam was about 100 Gray.

Immediately after irradiation, a reddish color pattern. was visible. Scanning with an optical scanning system produced planar acquisition images of the optical density distribution, as represented by the image shown in FIG. 2.

Figure 2:
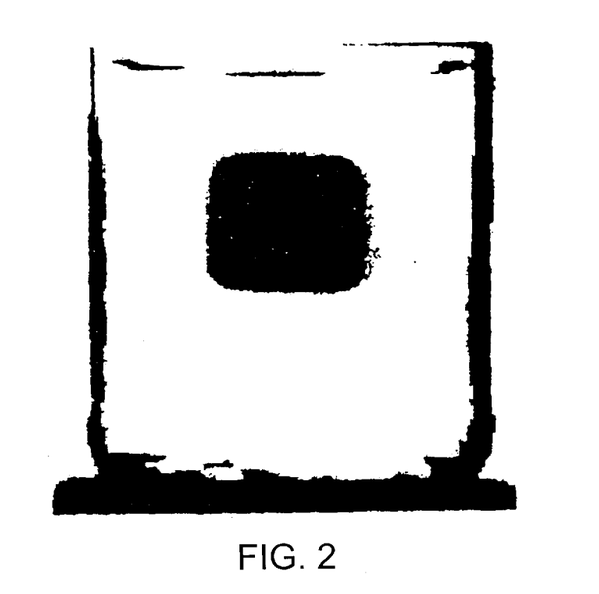
FIG. 2 depicts a plan view of the color distribution pattern of an optically scanned image.
Figure 3:
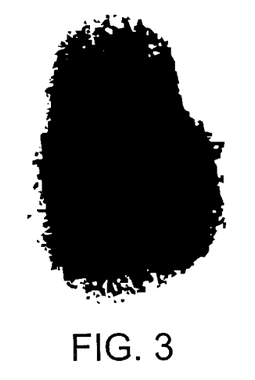
FIG. 3 shows a plan view of transverse tomographic reconstruction through the center of the distribution, illustrated in FIG. 2.

Referring to FIG. 3, a transverse tomographic reconstruction through the center of the distribution of FIG. 2 is shown.

Figure 4:
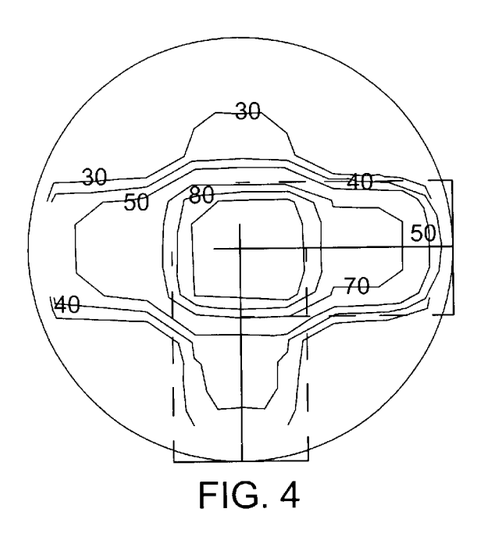
FIG. 4 depicts a schematic view of the predicted radiation dose distribution produced by a clinical treatment-planning computer (Cadplan), of the image illustrated in FIGS. 2 and 3.

Referring to FIG. 4, the predicted radiation dose distribution produced by a clinical treatment-planning computer (Cadplan) is illustrated.

Figure 5:
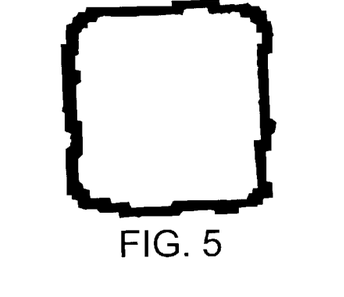
FIGS. 5 and 6 illustrate in plan views, respectively, the isocontours for the distribution of FIG. 4, after 2.5 hours and 5 weeks post-irradiation storage at 2 degrees Celsius.
Figure 6:
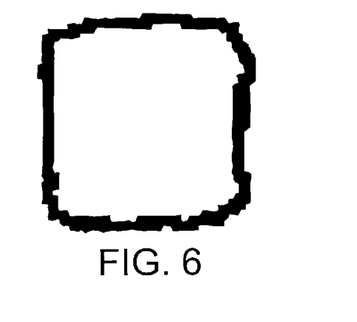

Referring to FIGS. 5 and 6, respective isocontours for the distribution of FIG. 4 is depicted, after 2.5 hours and 5 weeks post-irradiation storage, at 2 degrees C.

Figure 7:
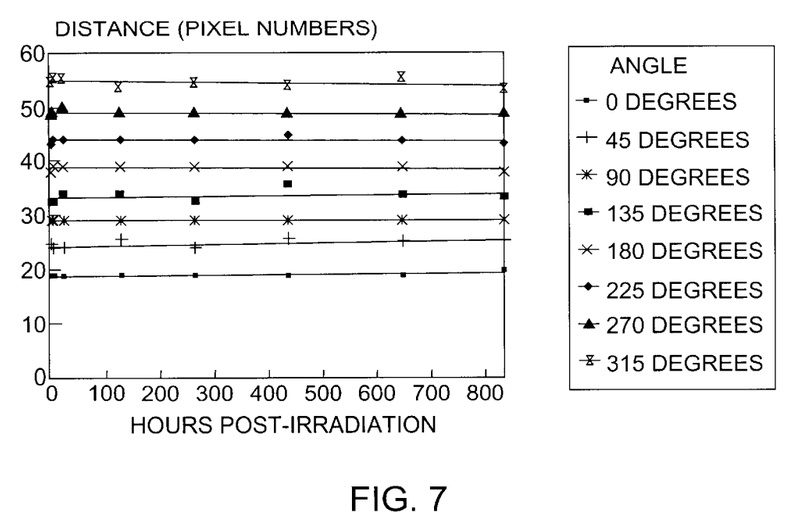
FIG. 7 depicts a graphical view of distance from the geometrical center to the 80% isocontour (expressed as numbers of pixel dimensions) of the isocontour images of FIGS. 5 and 6, at eight angles, as a function of post-irradiation storage time.

Referring to FIG. 7, a graph is shown presenting the distance from the geometrical center to the 80% isocontour expressed as numbers of pixel dimensions, at eight angles, as a function of post-irradiation storage time (One pixel is about 0.8 mm).

Figure 8:
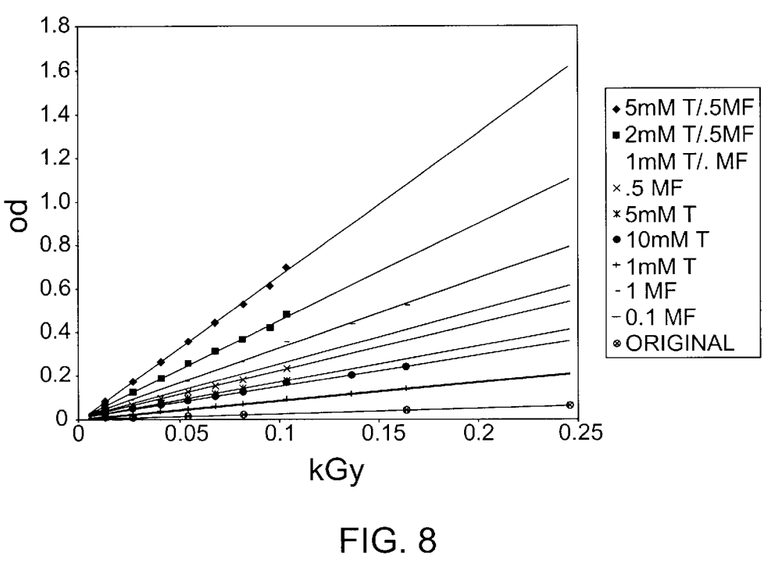
FIG. 8 illustrates a graphical view of absorption at a wavelength of 525 nm versus dosage for gels containing NBTZ and different concentrations of Triton X100 and/or sodium formate.

FIG. 1 shows the system is linear with dose in the range of approximately between 15 Cray to at least 800 Gray while FIG. 8 indicates that linearity can be found to at least 5.4 Gray and may still extend to lower values. The lower values in this range are employed clinically in radiation-therapy, therefore, this methodology allows for a means of simulating actual potential radiation therapies to determine target site and diffusion of irradiation within the body of the patient. It is likely that, with modifications, aqueous tetrazolium based gel systems could be made useful in even lower dose ranges. For example, this particular tetrazolium compound may not necessarily be the most radiation sensitive of the more than 240 known in the literature.

Also, sensitivity is dependent on the ratio of "signal" (formazan absorption) to "noise", which includes tetrazolium optical absorption at the measurement wavelength. The data obtained thus far on the effect of NBTZ concentration, as illustrated in FIG. 1, suggests that the radiation chemical yield of the colored formazan product increases as NBTZ concentration increases, but not necessarily linearly however, the NBTZ absorption at 525 nm ("noise") does increases in proportion to NBTZ concentration. In the present invention concentations of NBTZ in the range of 0.1 to 100 mM are useful. Preferred concentrations of NBTZ range from 0.5 to 20 mM and most preferred concentrations of NBTZ range from 1 to 10 mM. These ranges will be dependent on the nature and quantity of various adjuvants as described elsewhere within this disclosure.

FIGS. 4, 5 and 6 demonstrate the excellent match of the image reconstruction contours with the treatment plan and with each other. Stability of the image is very important for those situations in which early imaging is not possible, or if the imaging must be repeated at a later time. The relative instability of images from ferrous-based gel systems may-limit their acceptance for clinical applications in such a case. Comparison of the isocontours derived 2.5 hours after irradiation (FIG. 5) with those measured after several weeks of storage (FIG. 6) shows the lack of apparent degradation of the formazan image over this time period. FIG. 7 is a quantification of this observation. The distance (in pixel units) from the center of the distribution to the 80% isocontour; at eight angles, was measured. These distances are plotted as a function of duration of post-irradiation storage at 2 degrees C. (For clarity of presentation the data for 90, 135, 180, 225, 270 and 315 degree angles have been offset by 10, 10, 20, 20, 30 and 30 pixel units respectively.) The data shows upward trends averaging only 0.08 per day. This is not a significant difference from zero, within the scatter of the data.

The non-diffusing character of the radiation image provides the capability of imaging at low dose rates, such as are employed in brachytherapy, without degradation of the image during an extended irradiation period. This is a major advantage over ferrous-based aqueous dosimeter systems, especially for small radiation fields.

The resultant image is probably due to the formazan molecules, generated by free radical reactions from local radiation dose that become attached to the surfaces of the gelatin matrix. If so, the spatial resolution is limited by the mean diffusion distance of formazan molecules to attachment sites. This in turn will depend on the type and concentration of the polymer used.

For the experiments, overall spatial resolution is undoubtedly limited by the resolution of the optical scanner and image reconstruction techniques, but is, nonetheless, nominally of the order of 1 mm.

The major components of the system are non toxic, and the system is not dependent on the presence, or absence of dissolved oxygen, so preparation is simple, and waste disposal problems are minimized. These are major advantages over acrylamide-based systems for practical and routine use in a clinical setting.

The lack of significant dependence on oxygen concentration in the experiments is probably a consequence of the very high reaction rate constant of NBTZ with hydrated electrons, $k=7.3 \times 10^{10}$ (L mol$^{-1}$ s$^{-1}$)$^{10}$. Oxygen reacts with hydrated electrons with a rate constant of $1.9 \times 10^{10}$ (L mol$^{-1}$ s$^{-1}$) Since the overall reaction rates for competing reactions are given by the products of rate constant and molar concentration, 1 mM NBTZ would compete with oxygen in dissolved air ($2 \times 10^{-4}$ molar at room temperature) for reduction by hydrated electrons by a factor of $(7.3 \times 10^{10} \times 10^{-3})/(1.9 \times 10^{10} \times 2 \times 10^{-4})=19$. Since the experimental gels were heated to about 45 degrees C., during preparation the oxygen concentration would probably be lower than $2 \times 10^{-4}$ molar, making the factor of 19 a lower limit. It would be expected, that oxygen would become a factor only at much lower NBTZ concentrations, or at extremely high radiation doses, when a substantial portion of the NBTZ had been reduced.

Since other modifications and changes varied to fit particular operating requirements and environments will be apparent to those skilled in the art, the invention is not considered limited to the examples chosen for purposes of disclosure, and covers all changes and modifications which do not constitute departures from the true spirit and scope of this invention.

While there have been shown and described what are at present considered the preferred embodiments of the invention, it will be obvious to those skilled in the art that various changes and modifications may be made therein without departing from the scope of the invention as defined by the appended claims.

Having thus described the invention, what is desired to be protected by Letters Patent is presented in the subsequently appended claims.

What is claimed is:

1. A radiochromic method, comprising the steps of:
   a) preparing a gel formulation of predetermined dimensions, said gel formulation comprising an aqueous soluble, color forming tetrazolium containing compound and wherein said aqueous soluble, color forming tetrazolium containing compound is of a type and of sufficient concentration to react rapidly with hydrated electrons to form a stable formazan colorant; and
   b) irradiating said gel formulation with at least one beam of irradiation having a cross-sectional area smaller than said gel formulation dimensions and of sufficient dosage to form an essentially permanent and insoluble colored product within said gel formulation.

2. The radiochromic method as recited in claim 1, where said gel formulation is in the form of a three dimensional object comprising an array of voxels, said irradiation is provided to said object from at least one of the three said dimensions and said insoluble colored product provides a measurable optical density within at least a portion of said voxels.

3. The radiochromic method as recited in claim 1, where the intensity of said beam is modulated temporally by adjusting the cross-section of the impinging beam or by applying the beam intermittently.

4. The radiochromic method as recited in claim 2, comprising the additional step of providing said irradiation beam in a scanned pattern in order to irradiate at least a portion of said voxels.

5. The radiochromic method as recited in claim 2, where the method further comprises analyzing the color intensity or optical density of each said voxel in order to determine the irradiation dosage absorbed by each said voxel.

6. The radiochromic method as recited in claim 1, were said irradiation comprises alpha and beta particles, gamma, cosmic, and X-rays, electron beam, and near and far ultra violet radiation.

7. The radiochromic method as recited in claim 1, where the impinging irradiation dose on said gel formulation is between about 10 and 1000 Gray.

8. The radiochromic method as recited in claim 1, where said gel formulation comprises gelatin or agrose.

9. A radiochromic method comprising the steps of:
   a) preparing a gel formulation comprising an aqueous soluble, color forming compound;
   b) applying a tagged or radiolabelled polymer comprising a mixture of components to said gel formulation in at least one predetermined area;
   c) utilizing a chromatographic technique to spatially separate said components;
   d) allowing sufficient time for said radiolabel from said spatially separated components to impart sufficient ionizing radiation to induce a chemical change to said color forming compound in the vicinity of said spatially separated components, said chemical change causing a change in solubility and color; and
   e) visualizing and quantifying the intensity of the color or the optical density in order to determine the number of said components and their physical quantity within said gel formulation.

10. The radiochromic method as recited in claim 9 where said chromatographic technique is electrophoresis.

11. The radiochromic method as recited in claim 9 where said polymer is a protein or a polynucleotide.

12. The radiochromic method as recited in claim 9, where said gel formulation comprises gelatin or agrose.

13. The radiochromic method as recited in claim 9, where said color forming compound comprises a tetrazolium 3 salt.

14. The radiochromic method as recited in claim 9, where said radiolabel comprises $^{3}$H, $^{14}$C, $^{32}$P, $^{33}$P, $^{35}$S, or 125I.

15. The radiochromic method as recited in claim 1, further comprising the step of:
   a) adding a surfactant to said gel formulation prior to said irradiation in an amount sufficient to cause micelle formation.

16. The radiochromic method as recited in claim 15, wherein said surfactant is a nonionic or cationic surfactant.

17. The radiochromic method as recited in claim 1, further comprising the step of:
   a) adding an effective amount of a hydroxy radical quencher prior to said irradiation to essentially prevent unwanted side reactions of hydroxy radicals or its subsequent derivatives from reducing the yield of said colored, insoluble product in said radiochromic method.

18. The radiochromic method as recited in claim 15, further comprising the step of:
   a) adding an effective amount of a hydroxy radical quencher prior to said irradiation to essentially prevent unwanted side reactions of hydroxy radicals or its subsequent derivatives from reducing the yield of said colored, insoluble product in said radiochromic method.

19. The radiochromic method as recited in claim 18, wherein the radiochromic process comprises converting soluble, colorless tetrazolium salts into insoluble colored formazan derivatives.

20. The radiochromic method as recited in claim 19, wherein the hydroxy radical quencher is selected from the group of alkanes, alkenes, alcohols, ethers, and mercaptans and derivatives thereof.

21. The radiochromic method as recited in claim 20, wherein said alcohol is an polyethoxylated alkyl phenol.

22. The radiochromic method as recited in claim 18, wherein said hydroxy radical quencher is a salt of an alkyl carboxylic acid.

23. The radiochromic method as recited in claim 22, wherein said alkyl carboxylic acid salt is sodium formate.

24. The radiochromic method as recited in claims 21, further comprising sodium formate.

25. A radiochromic method, comprising the steps of:
   a) preparing a gel formulation of predetermined dimensions, said gel formulation comprising an aqueous soluble, color forming compound consisting essentially of a tetrazolium 3 salt; and
   b) irradiating said gel formulation with at least one beam of irradiation having a cross-sectional area smaller than said gel formulation dimensions and of sufficient dosage to form an permanent and insoluble colored product within said gel formulation.

* * * * *